United States Patent
Hickey

(10) Patent No.: US 6,174,919 B1
(45) Date of Patent: Jan. 16, 2001

(54) CYANOACRYLATE COMPOSITIONS WITH VINYL TERMINATED ESTER GROUPS

(75) Inventor: Timothy P. Hickey, Raleigh, NC (US)

(73) Assignee: Closure Medical Corporation, Raleigh, NC (US)

( * ) Notice: Under 35 U.S.C. 154(b), the term of this patent shall be extended for 0 days.

(21) Appl. No.: 09/025,473

(22) Filed: Feb. 18, 1998

(51) Int. Cl.$^7$ .................................................. A01N 37/34
(52) U.S. Cl. ........................ 514/519; 156/326; 156/330.9; 424/400; 424/443; 424/448; 424/487
(58) Field of Search .................................. 424/400, 443, 424/448, 487; 156/330.9, 326

(56) References Cited

U.S. PATENT DOCUMENTS

| | | |
|---|---|---|
| 2,721,858 | 10/1955 | Joyner et al. . |
| 3,254,111 | 5/1966 | Hawkins et al. . |
| 3,554,990 | 1/1971 | Quinn et al. . |
| 3,940,362 | 2/1976 | Overhults . |
| 3,975,422 | 8/1976 | Buck . |
| 3,995,641 | 12/1976 | Kronenthal et al. . |
| 4,041,062 | 8/1977 | Buck . |
| 4,127,382 | 11/1978 | Perry . |
| 4,134,929 | 1/1979 | Stoakley et al. . |
| 4,136,138 | 1/1979 | Dombroski et al. . |
| 4,364,876 | 12/1982 | Kimura et al. . |
| 4,720,513 | * 1/1988 | Kameyama et al. .................. 523/203 |
| 5,259,835 | 11/1993 | Clark et al. . |
| 5,328,687 | 7/1994 | Leung et al. . |
| 5,480,935 | * 1/1996 | Greff et al. .......................... 524/776 |
| 5,514,371 | 5/1996 | Leung et al. . |
| 5,514,372 | 5/1996 | Leung et al. . |
| 5,575,997 | 11/1996 | Leung et al. . |
| 5,582,834 | 12/1996 | Leung et al. . |
| 5,624,669 | 4/1997 | Leung et al. . |

FOREIGN PATENT DOCUMENTS

| | | |
|---|---|---|
| 1527561 | 10/1978 | (GB) . |
| WO 97/31598 | 9/1997 | (WO) . |

* cited by examiner

*Primary Examiner*—Thurman K. Page
*Assistant Examiner*—P. Kulkosky
(74) *Attorney, Agent, or Firm*—Oliff & Berridge, PLC

(57) ABSTRACT

An adhesive composition includes compounds having the following formula:

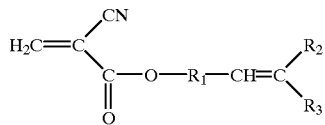

wherein $R_1$ is alkyl, alkoxy alkyl, anhydride, ether, ester, or amide, and $R_2$ and $R_3$ are hydrogen, alkyl, alkoxy alkyl, hydroxy, alkenyl, ester, carboxylic acid or ether and wherein $R_1$ is optionally omitted where $R_2$ and $R_3$ are not both hydrogen.

19 Claims, No Drawings

CYANOACRYLATE COMPOSITIONS WITH VINYL TERMINATED ESTER GROUPS

BACKGROUND OF THE INVENTION

1. Field of Invention

The present invention is directed to monomer compositions useful to form industrial, consumer or medical adhesives and sealants, and methods of applying such compositions. More particularly, this invention relates to monomeric cyanoacrylate compositions having vinyl terminated ester groups that allow a biologically acceptable method of cross-linking through the vinyl group.

2. Description of Related Art

U.S. Pat. No. 5,624,669 to Leung et al., discloses hemostatic procedures for sealing punctures and incisions in blood vessels and internal organs by applying a cyanoacrylate monomer. Although the cyanoacrylate may polymerize and/or cross-link in vivo, it preferably does so without the need for external sources of physical initiation such as irradiation.

U.S. Pat. No. 4,134,929 to Stoakley et al. discloses a polymerizable monomeric allyl 2-cyanoacrylate containing portion comprising an amount of an organic peroxide free radical providing compound sufficient to cause crosslinking of a difunctional monomer diester with the allyl 2-cyanoacrylate. Stoakley discloses that crosslinking may occur by way of the allyl group.

U.S. Pat. No. 4,136,138 to Dombroski et al. discloses a polymerizable monomeric 2-cyanoacrylate containing portion comprising an amount of an organic peroxide free radical providing compound sufficient to cause crosslinking of a difunctional monomer diester with the 2-cyanoacrylate. Dombroski discloses that the allyl 2-cyanoacrylate-based adhesive compositions are especially useful as dental adhesives.

U.S. Pat. No. 3,975,422 to Buck discloses difunctional monomers where R is an organic linking group derived from a diol or a dihalide of the formula X—R—X, where X is either Cl, Br, I, or hydroxy. The difunctional monomers are employed as crosslinking agents for monofunctional esters of 2-cyanoacrylates. The monofunctional cyanoacrylate monomers may be cyanoacrylates that are terminated by an alkyl, cyclohexyl or phenyl group. Copolymerized compositions of the monomer blends (difunctional and monofunctional) are useful as adhesives in dental applications. The polymerization of these compositions is initiated by an anionic catalyst or by thermal or other means.

SUMMARY OF THE INVENTION

The present invention is directed to monomeric cyanoacrylate compositions having vinyl terminated ester groups that cross-link through the vinyl group, and biomedical uses of such compositions. Cross-linking occurs by way of the vinyl terminated ester groups. In embodiments, chemical durability, flexibility and elasticity of the resulting polymers or copolymers may be increased and degradability can be reduced. In addition, in embodiments high temperatures or ultraviolet initiators may not be needed for cross-linking.

DETAILED DESCRIPTION OF PREFERRED EMBODIMENTS

Cyanoacrylate adhesive compositions of the invention contain compounds represented by the following formula (I):

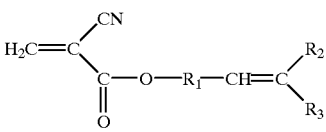

wherein $R_1$ is alkyl, alkoxy, anhydride, ether, ester, or amide, and $R_2$ and $R_3$ are independently alkyl, alkoxy, hydrogen, hydroxy, alkenyl, ester, carboxylic acid, ether, or electron withdrawing groups such as halogens, amides, cyanos, esters, acids and ethers. Preferably, $R_1$ is an alkyl having from about 1 to 8 carbon atoms. Preferably, $R_2$ and $R_3$ are hydrogen atoms. More preferably, $R_2$ and $R_3$ are alkyl groups having from about 1 to 3 carbon atoms. The $R_1$ group extends the distance of the $R_2$ and $R_3$ groups away from the carbonyl group, thereby making them more chemically accessible and improving chemical durability, flexibility and elasticity of a polymer comprising the monomer. In embodiments, $R_1$ may be omitted if $R_2$ and $R_3$ are not both hydrogen.

In embodiments, the adhesive compositions may additionally contain heat and/or light (e.g., visible or ultraviolet light) activated initiators and accelerators that initiate cross-linking of the cyanoacrylate compounds.

Particular initiators for particular systems may be readily selected by one of ordinary skill in the art without undue experimentation. Suitable polymerization initiators for the cyanoacrylate compositions include, but are not limited to, detergent compositions; surfactants: e.g., nonionic surfactants such as polysorbate 20 (e.g., Tween 20™), polysorbate 80 (e.g., Tween 80™) and poloxamers, cationic surfactants such as tetrabutylammonium bromide, anionic surfactants such as benzalkonium chloride or its pure components, stannous octoate (tin (II) 2-ethylheaxanoate), and sodium tetradecyl sulfate, and amphoteric or zwitterionic surfactants such as dodecyldimethyl(3-sulfopropyl)ammonium hydroxide, inner salt; amines, imines and amides, such as imidazole, tryptamine, urea, arginine and povidine; phosphines, phosphites and phosphonium salts, such as triphenylphosphine and triethyl phosphite; alcohols such as ethylene glycol, methyl gallate, ascorbic acid, tannins and tannic acid; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat 336; and organometallics such as cobalt naphthenate and manganese acetylacetonate and radical initiators.

Suitable initiators for both of the polymerization of the cyanoacrylate and cross-linking of the vinyl group of the composition include, but are not limited to, radicals, such as di-t-butyl peroxide, azobisisobutyronitrile and benzoylperoxide and sodium bisulfite. The polymerizable and/or cross-linkable material may also contain an initiator which is inactive until activated by a catalyst or accelerator (included within the scope of the term "initiator" as used herein). Accelerators for radical initiators such as dimethylaminopyridine and other aminopyridine type molecules may act as an initiator for the cyanoacrylate as well as for the radical polymerization of the vinyl moiety.

In embodiments, when $R_1$ is omitted and $R_2$ and/or $R_3$ are a moiety other than hydrogen, and the composition is to be cationically polymerizable, materials such as strong acids, alkyl iodides (iodomethane), iodine, acetyl perchlorate, and Lewis acids (boron trifluoride, tin tetrachloride, aluminum trichloride, and organometallic derivatives, e.g., $RAlCl_2$, $R_2AlCl$, wherein R is an alkyl group and $R_2$ is two R groups) may be used.

The monomer compositions of the present invention and polymers formed therefrom are useful as tissue adhesives, sealants for preventing bleeding or for covering open wounds, and in other biomedical applications. They find uses in, for example, apposing surgically incised or traumatically lacerated internal and/or external tissues; setting fractured bone structures; retarding blood flow from wounds; drug delivery; dressing burns; and aiding repair and regrowth of living tissue.

Conventional surgical adhesive compositions have included plasticizers with the adverse effect of reducing the film strength. It has been discovered that, contrary to prior belief, the film strength (e.g., toughness) under certain conditions is not adversely reduced upon the addition of greater amounts of plasticizing agent. Depending on the particular acidic stabilizing agent and the purity of the monomer utilized in the adhesive composition, the addition of greater amounts of plasticizing agent may increase the toughness of the resulting bond formed on the wound. Acidic stabilizing agents do not significantly affect the polymerization of the monomer in the present composition and provide increased film strength with increasing amounts of plasticizing agents.

Monomers that may be used in this invention are polymerizable, e.g. anionically polymerizable or free radical polymerizable, to form polymers. In embodiments, the cyanoacrylate composition may comprise a homopolymer of the monomer of formula (I) or a copolymer or terpolymer with other monomers. Such other monomers include, but are not limited to, acrylate monomers, methacrylate monomers, and 1,1-disubstituted ethylene monomers of the formula:

$$HRC=CXY \quad (II)$$

wherein X and Y are each strong electron withdrawing groups, and R is H, —CH=CH$_2$, or an alkyl such as methyl, ethyl and other lower alkyls such as butyl and the like, provided that X and Y are both cyano groups, a $C_1$–$C_4$ alkyl group.

Examples of monomers within the scope of formula (II) include alpha-cyanoacrylates, vinylidene cyanides, $C_1$–$C_4$ alkyl homologues of vinylidene cyanides, dialkyl methylene malonates, acylacrylonitriles, vinyl sulfinates and vinyl sulfonates of the formula $H_2C=CX'Y'$ wherein X' is —SO$_2$R' or —SO$_3$R' and Y' is —CN, —COOR', —COCH$_3$, —SO$_2$R' or —SO$_3$R', and R' is H or hydrocarbyl.

Preferred monomers of formula (II) for use in this invention are alpha-cyanoacrylates. These monomers are known in the art and have the formula

(III)

wherein $R^2$ is hydrogen or lower alkyl and $R^3$ is a hydrocarbyl or substituted hydrocarbyl group including polymeric groups; a group having the formula —$R^4$—O—$R^5$—O—$R^6$, wherein $R^4$ is a 1,2-alkylene group having 2–4 carbon atoms, $R^5$ is an alkylene group having 2–4 carbon atoms, and $R^6$ is an alkyl group having 1–6 carbon atoms; or a group

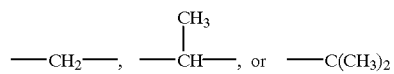

wherein n is 1–10, preferably 1–5 carbon atoms and $R^8$ is an organic moiety.

Examples of suitable hydrocarbyl and substituted hydrocarbyl groups include straight chain or branched chain alkyl groups having 1–16 carbon atoms; straight chain or branched chain $C_1$–$C_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic moiety $R^8$ may be substituted or unsubstituted and may be straight chain, branched or cyclic, saturated, unsaturated or aromatic. Examples of such organic moieties include $C_1$–$C_8$ alkyl moieties, $C_2$–$C_8$ alkenyl moieties, $C_2$–$C_8$ alkynyl moieties, $C_3$–$C_{12}$ cycloaliphatic moieties, aryl moieties such as phenyl and substituted phenyl and aralkyl moieties such as benzyl, methylbenzyl and phenylethyl. Other organic moieties include substituted hydrocarbon moieties, such as halo (e.g., chloro-, fluoro- and bromo-substituted hydrocarbons) and oxy- (e.g., alkoxy substituted hydrocarbons) substituted hydrocarbon moieties. Preferred organic moieties are alkyl, alkenyl and alkynyl moieties having from 1 to about 8 carbon atoms, and halo-substituted derivatives thereof. Particularly preferred are alkyl moieties of 4 to 6 carbon atoms.

In the cyanoacrylate monomer of formula (III), $R^3$ is preferably an alkyl group having 1–10 carbon atoms or a group having the formula —AOR$^9$, wherein A is a divalent straight or branched chain alkylene or oxyalkylene moiety having 2–8 carbon atoms, and $R^9$ is a straight or branched alkyl moiety having 1–8 carbon atoms.

Examples of groups represented by the formula —AOR$^9$ include 1-methoxy-2-propyl, 2-butoxy ethyl, isopropoxy ethyl, 2-methoxy ethyl, and 2-ethoxy ethyl.

The preferred alpha-cyanoacrylate monomers used in this invention are 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate.

The alpha-cyanoacrylates of formula (III) can be prepared according to methods known in the art. Reference is made, for example, to U.S. Pat. Nos. 2,721,858 and 3,254,111, each of which is hereby incorporated by reference herein. For example, the alpha cyanoacrylates can be prepared by reacting an alkyl cyanoacetate with formaldehyde in a non-aqueous organic solvent and in the presence of a basic catalyst, followed by pyrolysis of the anhydrous intermediate polymer in the presence of a polymerization inhibitor. The alpha-cyanoacrylate monomers prepared with low moisture content and essentially free of impurities are preferred for biomedical use.

The alpha-cyanoacrylates of formula (III) wherein $R^3$ is a group having the formula —$R^4$—O—$R^5$—O—$R^6$ can be prepared according to the method disclosed in U.S. Pat. No. 4,364,876 to Kimura et al., which is hereby incorporated by reference herein. In the Kimura et al. method, the alpha-cyanoacrylates are prepared by producing a cyanoacetate by esterifying cyanoacetic acid with an alcohol or by transesterifying an alkyl cyanoacetate and an alcohol; condensing the cyanoacetate and formaldehyde or para-formaldehyde in the presence of a catalyst at a molar ratio of 0.5–1.5:1, preferably 0.8–1.2:1, to obtain a condensate; depolymerizing the condensation reaction mixture either directly or after removal of the condensation catalyst to yield crude cyanoacrylate; and distilling the crude cyanoacrylate to form a high purity cyanoacrylate.

The alpha-cyanoacrylates of formula (III) wherein $R^3$ is a group having the formula

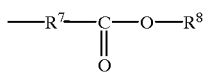

can be prepared according to the procedure described in U.S. Pat. No. 3,995,641 to Kronenthal et al., which is hereby incorporated by reference herein. In the Kronenthal et al. method, such alpha-cyanoacrylate monomers are prepared by reacting an alkyl ester of an alpha-cyanoacrylic acid with a cyclic 1,3-diene to form a Diels-Alder adduct which is then subjected to alkaline hydrolysis followed by acidification to form the corresponding alpha-cyanoacrylic acid adduct. The alpha-cyanoacrylic acid adduct is preferably esterified by an alkyl bromoacetate to yield the corresponding carbalkoxymethyl alpha-cyanoacrylate adduct. Alternatively, the alpha-cyanoacrylic acid adduct may be converted to the alpha-cyanoacrylyl halide adduct by reaction with thionyl chloride. The alpha-cyanoacrylyl halide adduct is then reacted with an alkyl hydroxyacetate or a methyl substituted alkyl hydroxyacetate to yield the corresponding carbalkoxymethyl alpha-cyanoacrylate adduct or carbalkoxy alkyl alpha-cyanoacrylate adduct, respectively. The cyclic 1,3-diene blocking group is finally removed and the carbalkoxy methyl alpha-cyanoacrylate adduct or the carbalkoxy alkyl alpha-cyanoacrylate adduct is converted into the corresponding carbalkoxy alkyl alpha-cyanoacrylate by heating the adduct in the presence of a slight deficit of maleic anhydride.

Examples of monomers of formula (III) include cyanopentadienoates and alpha-cyanoacrylates of the formula:

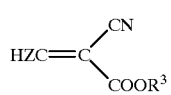

wherein Z is —CH=CH$_2$ and $R^3$ is as defined above. The monomers of formula (IV) wherein $R^3$ is an alkyl group of 1–10 carbon atoms, i.e., the 2-cyanopenta-2,4-dienoic acid esters, can be prepared by reacting an appropriate 2-cyanoacetate with acrolein in the presence of a catalyst such as zinc chloride. This method of preparing 2-cyanopenta-2,4-dienoic acid esters is disclosed, for example, in U.S. Pat. No. 3,554,990, which is hereby incorporated by reference herein.

Preferred monomers are alkyl alpha-cyanoacrylates and more preferably octyl alpha-cyanoacrylates, especially 2-octyl alpha-cyanoacrylate. Monomers utilized in the present application should be very pure and contain few impurities (e.g., surgical grade).

Compositions of the present invention may include at least one plasticizing agent that imparts flexibility to the polymerized monomer formed on the wound or incision. The plasticizing agent preferably contains little or no moisture and should not significantly affect the polymerization of the monomer.

Other compositions are exemplified by U.S. Pat. Nos. 5,259,835 and 5,328,687 and U.S. patent applications Ser. Nos. 08/609,921, 08/714,288, 08/909,845, 08/755,007, 08/920,876, and 08/488,411, all incorporated by reference herein in their entirety.

Examples of suitable plasticizers include acetyl tributyl citrate, dimethyl sebacate, triethyl phosphate, tri(2-ethylhexyl)phosphate, tri(p-cresyl)phosphate, glyceryl triacetate, glyceryl tributyrate, diethyl sebacate, dioctyl adipate, isopropyl myristate, butyl stearate, lauric acid, trioctyl trimellitate, dioctyl glutarate and mixtures thereof. Preferred plasticizers are tributyl citrate and acetyl tributyl citrate. In embodiments, suitable plasticizers include polymeric plasticizers, such as polyethylene glycol (PEG) esters and capped PEG esters or ethers, polyester glutarates and polyester adipates.

Compositions of the present invention may also include at least one acidic stabilizing agent that inhibits polymerization. Such stabilizing agents may also include mixtures of anionic stabilizing agents and radical stabilizing agents.

Examples of suitable anionic stabilizing agents include, but are not limited to, sultones (e.g., α-chloro-α-hydroxy-o-toluenesulfonic acid-γ-sultone), sulfur dioxide, sulfuric acid, sulfonic acid, sulfurous acid, lactone, boron trifluoride, organic acids, alkyl sulfate, alkyl sulfite, 3-sulfolene, alkylsulfone, alkyl sulfoxide, mercaptan, and alkyl sulfide and mixtures thereof. Preferable anionic stabilizing agents are acidic stabilizing agents of organic acids such as acetic acid or phosphoric acid. In embodiments, the amount of sulfur dioxide stabilizer is less than 100 ppm, preferably 5–75 ppm, and more preferably from about 20–50 ppm. The amount of sultone and/or trifluoroacetic acid is about 500–3000 ppm.

Examples of suitable radical stabilizing agents include hydroquinone, hydroquinone monomethyl ether, catechol, pyrogallol, benzoquinone, 2-hydroxybenzoquinone, p-methoxy phenol, t-butyl catechol, butylated hydroxy anisole, butylated hydroxy toluene, and t-butyl hydroquinone.

Suitable acidic stabilizing agents include those having aqueous $pK_a$ ionization constants ranging from −12 to 7, preferably from about −3.5 to about 6, and more preferably from about 2 to about 5.5. For example, suitable acidic stabilizing agents include: hydrogen sulfide ($pK_a$ 7.0), carbonic acid ($pK_a$ 6.4), triacetylmethane ($pK_a$ 5.9), acetic acid ($pK_a$ 4.8), benzoic acid ($pK_a$ 4.2), 2,4-dinitrophenol ($pK_a$ 4.0), formic acid ($pK_a$ 3.7), nitrous acid ($pK_a$ 3.3), hydrofluoric acid ($pK_a$ 3.2), chloroacetic acid ($pK_a$ 2.9), phosphoric acid ($pK_a$ 2.2), dichloroacetic acid ($pK_a$ 1.3), trichloroacetic acid ($pK_a$ 0.7), 2,4,6-trinitrophenol (picric acid) ($pK_a$ 0.3), trifluoroacetic acid ($pK_a$ 0.2), sulfuric acid ($pK_a$ −3.0), and mixtures thereof.

When adding the above-mentioned acidic stabilizing agents to the adhesive composition, the addition of plasticizing agents in amounts ranging from about 0.5 wt. % to about 16 wt. %, preferably from about 3 wt. % to about 9 wt. %, and more preferably from about 5 wt. % to about 7 wt. % provides increased film strength (e.g., toughness) in the polymerized monomer over polymerized monomers having amounts of plasticizing agents and acidic stabilizing agents outside of the above ranges.

The concentration of the acidic stabilizing agents utilized may vary depending on the strength of the acid. For example, when using acetic acid, a concentration of 80–200 ppm (wt/wt), preferably 90–180 ppm (wt/wt), and more preferably 100–150 ppm (wt/wt) may be utilized. When using a stronger acid such as phosphoric acid, a concentration range of 20–80 ppm (wt/wt), preferably, 30–70 ppm (wt/wt) and more preferably 40–60 ppm (wt/wt) may be utilized. In embodiments, the amount of trifluoroacetic acid is about 100 to 3000 ppm, preferably 500–1500 ppm. In other embodiments, the amount of phosphoric acid is about 10–200 ppm, preferably about 50–150 ppm, and more preferably about 75–125 ppm.

Other compositions are exemplified by U.S. Pat. Nos. 5,624,669, 5,582,834, 5,575,997, 5,514,371, 5,514,372, 5,259,835 and 5,328,687, incorporated by reference herein in their entirety. The compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites; ammonium sulfite salts; amines; amides; imides; nitriles; carbamates; alcohols; mercaptans; proteins; mixtures of amines, amides, and proteins; active methylene compounds such as cyclic ketones and compounds having a b-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom.

Bisulfites and sulfites useful as the formaldehyde scavenger compound in this invention include alkali metal salts such as lithium, sodium and potassium salts, and ammonium salts, for example, sodium bisulfite, potassium bisulfite, lithium bisulfite, ammonium bisulfite, sodium sulfite, potassium sulfite, lithium sulfite, ammonium sulfite, and the like.

Examples of amines useful in this invention include the aliphatic and aromatic amines such as, for example, aniline, benzidine, aminopyrimidine, toluene-diamine, triethylenediamine, diphenylamine, diaminodiphenylamine, hydrazines and hydrazide.

Suitable proteins include collagen, gelatin, casein, soybean protein, vegetable protein, keratin and glue. The preferred protein for use in this invention is casein.

Suitable amides for use in this invention include urea, cyanamide, acrylamide, benzamide, and acetamide. Urea is a preferred amide.

Suitable alcohols include phenols, 1,4-butanediol, d-sorbitol, and polyvinyl alcohol.

Examples of suitable compounds having a b-dicarbonyl group include malonic acid, acetylacetone, ethylacetone, acetate, malonamide, diethylmalonate or another malonic ester.

Preferred cyclic ketones for use in this invention include cyclohexanone or cyclopentanone.

Examples of suitable heterocyclic compounds for use as the formaldehyde scavenger in this invention are disclosed, for example, in U.S. Pat. No. 4,127,382 (Perry) which is hereby incorporated by reference herein. Such heterocyclic compounds include, for example, benzimidazole, 5-methyl benzimidazole, 2-methylbenzimidazole, indole, pyrrole, 1,2, 4-triazole, indoline, benzotriazole, indoline, and the like.

A preferred formaldehyde scavenger for use in this invention is sodium bisulfite.

In practicing the present invention, the formaldehyde concentration reducing agent, e.g., formaldehyde scavenger compound, is added in an effective amount to the cyanoacrylate. The "effective amount" is that amount sufficient to reduce the amount of formaldehyde generated during subsequent in vivo biodegradation of the polymerized cyanoacrylate. This amount will depend on the type of active formaldehyde concentration reducing agent, and can be readily determined without undue experimentation by those skilled in the art.

The formaldehyde concentration reducing agent may be used in this invention in either free form or in microencapsulated form. Other compositions are exemplified by U.S. patent application Ser. No. 08/714,288, incorporated by reference herein in their entirety.

When microencapsulated, the formaldehyde concentration reducing agent is released from the microcapsule continuously over a period of time during the in vivo biodegradation of the cyanoacrylate polymer.

For purposes of this invention, the microencapsulated form of the formaldehyde concentration reducing agent is preferred because this embodiment prevents or substantially reduces polymerization of the cyanoacrylate monomer by the formaldehyde concentration reducing agent, which increases shelf-life and facilitates handling of the monomer composition during use.

Microencapsulation of the formaldehyde scavenger can be achieved by many known microencapsulation techniques. For example, microencapsulation can be carried out by dissolving a coating polymer in a volatile solvent, e.g., methylene chloride, to a polymer concentration of about 6% by weight; adding a formaldehyde scavenger compound in particulate form to the coating polymer/solvent solution under agitation to yield a scavenger concentration of 18% by weight; slowly adding a surfactant-containing mineral oil solution to the polymer solution under rapid agitation; allowing the volatile solvent to evaporate under agitation; removing the agitator; separating the solids from the mineral oil; and washing and drying the microparticles. The size of the microparticles will range from about 0.001 to about 1000 microns.

The coating polymer for microencapsulating the formaldehyde concentration reducing agent should be polymers which undergo in vivo bioerosion, preferably at rates similar to or greater than the cyanoacrylate polymer formed by the monomer, and should have low inherent moisture content. Such "bioerosion" can occur as a result of the physical or chemical breakdown of the encapsulating material, for example, by the encapsulating material passing from solid to solute in the presence of body fluids, or by biodegradation of the encapsulating material by agents present in the body.

Examples of coating materials which can be used to microencapsulate the formaldehyde concentration reducing agent include polyesters, such as polyglycolic acid, polylactic acid, poly-1,4-dioxa-2-one, polyoxaltes, polycarbonates, copolymers of polyglycolic acid and polylactic acid, polycaprolactone, poly-b-hydroxybutyrate, copolymers of epsilon-caprolactone and delta-valerolactone, copolymers of epsilon-caprolactone and DL-dilactide, and polyester hydrogels; polyvinylpyrrolidone; polyamides; gelatin; albumin; proteins; collagen; poly(orthoesters); poly (anhydrides); poly(alkyl-2-cyanoacrylates); poly (dihydropyrans); poly(acetals); poly(phosphazenes); poly (urethanes); poly(dioxinones); cellulose; and starches.

Examples of the surfactant which can be added to the mineral oil include those commercially available under the designations Triton x-100, Tween 20 and Tween 80.

The composition of this invention may further contain one or more adjuvant substances, such as thickening agents, medicaments, or the like, to improve the medical utility of the monomer for particular medical applications.

Suitable thickeners include, for example, polycyanoacrylates, polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene. Examples of alkyl methylacrylates and acrylates are poly(2-ethylhexyl methacrylate) and poly(2-ethylhexyl acrylate), also poly (butylmethacrylate) and poly(butylacrylate), also copolymers of various acrylate and methacrylate monomers, such as poly(butyl methacrylate-co-methylacrylate).

To improve the cohesive strength of adhesives formed from the compositions of this invention, difunctional monomeric cross-linking agents may be added to the monomer compositions of this invention. Such crosslinking agents are known. Reference is made, for example, to U.S. Pat. No. 3,940,362 to Overhults, which is hereby incorporated by reference herein. Examples of suitable crosslinking agents include alkyl bis(2-cyanoacrylates), triallyl isocyanurates, alkylene diacrylates, alkylene dimethacrylates, trimethylol propane triacrylate, and alkyl bis(2-cyanoacrylates). A catalytic amount of an amine activated free radical initiator may be added to initiate polymerization of the cyanoacrylate monomer/crosslinking agent blend.

The compositions of this invention may further contain fibrous reinforcement and colorants, i.e., dyes and pigments. Examples of suitable fibrous reinforcement include PGA microfibrils, collagen microfibrils, cellulosic microfibrils, and olefinic microfibrils. Examples of suitable colorants include 1-hydroxy-4-[4-methylphenyl-amino]-9,10 anthracenedione (D+C violet No. 2); disodium salt of 6-hydroxy-5-[(4-sulfophenyl)axo]-2-naphthalene-sulfonic acid (FD+C Yellow No. 6); 9 -(o-carboxyphenyl)-6-hydroxy-2,4,5,7-tetraiodo-3H-xanthen-3-one, disodium salt, monohydrate (FD+C Red No. 3); 2-(1,3-dihydro-3-oxo-5-sulfo-2H-indol-2-ylidene)-2,3-dihydro-3-oxo-1H-indole-5-sulfonic acid disodium salt (FD+C Blue No. 2); and [phthalocyaninato (2-)] copper.

Depending on the particular requirements of the user, the adhesive compositions of this invention can be applied by known means such as with a swab, glass stirring rod, sterile brush or medicine dropper. However, in many situations a spray dispensing package is preferred in which the adhesive composition is in solution with a compatible anhydrous propellant. Other modes of application are exemplified in U.S. patent application Ser. No. 08/488,411, incorporated by reference herein in its entirety.

What is claimed is:

1. An adhesive composition with improved properties of chemical durability, flexibility and elasticity of resulting polymers and copolymers, comprising a compound of the following formula (I):

$$H_2C=C(CN)-C(=O)-O-R_1-CH=C(R_2)(R_3) \quad (I)$$

wherein $R_1$ is selected from the group consisting of alkyl having at least 2 carbon atoms, alkoxy, anhydride, ether, ester, and amide, wherein $R_2$ and $R_3$ are independently selected from the group consisting of hydrogen, alkyl, alkoxy, hydroxy, alkenyl, ester, carboxylic acid, ether and electron withdrawing groups, and wherein $R_1$ may also optionally be omitted or be an alkyl having 1 carbon atom when $R_2$ and $R_3$ are not both hydrogen.

2. The adhesive composition according to claim 1, wherein said electron withdrawing groups are selected from the group consisting of halogens, amides, cyanos, esters, acids and ethers.

3. The adhesive composition according to claim 1, wherein $R_1$ is an alkyl having from about 2 to 8 carbon atoms.

4. The adhesive composition according to claim 1, wherein $R_2$ and $R_3$ are hydrogen.

5. The adhesive composition according to claim 1, wherein $R_2$ and $R_3$ are alkyls having from 1 to 3 carbon atoms.

6. The adhesive composition according to claim 1, further comprising an initiator.

7. The adhesive composition according to claim 6, wherein said initiator is selected from the group consisting of benzalkonium chloride, stannous octoate and sodium tetradecyl sulfate.

8. The adhesive composition according to claim 1, further comprising a radical initiator.

9. The adhesive composition according to claim 8, wherein said radical initiator is selected from the group consisting of di-t-butyl peroxide, azobisisobutyronitrile and benzoylperoxide.

10. A method of joining together surfaces, comprising:
   (a) holding together at least two surfaces to form abutted surfaces, and
   (b) applying across said abutted surfaces an adhesive composition according to claim 1.

11. An adhesive composition comprising a homopolymer of the compound of claim 1.

12. An adhesive composition comprising a copolymer of the compound of claim 1 and a 1,1-disubstituted ethylene monomer.

13. The adhesive composition according to claim 12, wherein said ethylene monomer is n-butyl cyanoacrylate or 2-octyl cyanoacrylate.

14. The adhesive composition according to claim 1, wherein crosslinking occurs through the vinyl terminated ester group.

15. The adhesive composition according to claim 1, further comprising an ultraviolet initiator.

16. A method of treatment comprising using the adhesive composition of claim 1 in a biomedical application selected from the group consisting of drug delivery, burn treatment, setting fractured bone structures, retarding blood flow from wounds, aiding repair and regrowth of living tissue and apposing surgically incised or traumatically lacerated internal or external tissues.

17. The adhesive composition according to claim 1, further comprising at least one acidic stabilizing agent.

18. The adhesive composition according to claim 17, further comprising at least one radical stabilizing agent.

19. The adhesive composition according to claim 18, further comprising at least one plasticizing agent.

* * * * *